(12) United States Patent
Kutryk et al.

(10) Patent No.: US 9,072,723 B2
(45) Date of Patent: Jul. 7, 2015

(54) MEDICAL DEVICE WITH COATING THAT PROMOTES ENDOTHELIAL CELL ADHERENCE

(75) Inventors: Michael John Bradley Kutryk, Ontario (CA); Robert J. Cottone, Jr., Davie, FL (US); Stephen M. Rowland, Miami, FL (US)

(73) Assignee: ORBUS MEDICAL TECHNOLOGY INC, Fort Lauderdale, FL (US)

( * ) Notice: Subject to any disclaimer, the term of this patent is extended or adjusted under 35 U.S.C. 154(b) by 0 days.

(21) Appl. No.: 13/589,907

(22) Filed: Aug. 20, 2012

(65) Prior Publication Data

US 2013/0035755 A1  Feb. 7, 2013

Related U.S. Application Data

(63) Continuation of application No. 11/562,931, filed on Nov. 22, 2006, now abandoned, which is a continuation of application No. 10/832,106, filed on Apr. 26, 2004, now Pat. No. 7,803,183, which is a continuation of application No. 09/808,867, filed on Mar. 15, 2001, now Pat. No. 7,037,332.

(60) Provisional application No. 60/189,674, filed on Mar. 15, 2000, provisional application No. 60/201,789, filed on May 4, 2000.

(51) Int. Cl.
*A61F 2/06* (2013.01)
*A61K 38/39* (2006.01)
*A61L 27/08* (2006.01)
(Continued)

(52) U.S. Cl.
CPC .................. *A61K 38/39* (2013.01); *A61L 27/08* (2013.01); *A61L 27/227* (2013.01); *A61L 27/303* (2013.01); *A61L 27/44* (2013.01); *A61L 27/54* (2013.01); *A61L 29/103* (2013.01); *A61L 29/126* (2013.01); *A61L 29/16* (2013.01); *A61L 31/047* (2013.01); *A61L 31/084* (2013.01); *A61L 31/125* (2013.01); *A61L 31/16* (2013.01); *A61L 2300/256* (2013.01); *A61L 2300/416* (2013.01); *A61L 2300/422* (2013.01); *A61L 2300/606* (2013.01); *B82Y 30/00* (2013.01); *C12N 5/0692* (2013.01); *C12N 2510/00* (2013.01); *A61K 38/363* (2013.01); *A61K 39/39558* (2013.01); *C07K 16/2896* (2013.01); *C07K 2317/55* (2013.01)

(58) Field of Classification Search
CPC ........ A61L 27/08; A61L 27/227; A61L 27/44
USPC .............................. 623/1.4–1.49, 23.72–23.76
See application file for complete search history.

(56) References Cited

U.S. PATENT DOCUMENTS 5,674,192 A * 10/1997 Sahatjian et al. ............... 604/28
5,733,925 A * 3/1998 Kunz et al. ...................... 514/449
(Continued)

*Primary Examiner* — Alvin Stewart
(74) *Attorney, Agent, or Firm* — Ascenda Law Group PC

(57) ABSTRACT

The invention relates to a method for healing blood vessels by stimulating the formation of a confluent endothelial autologous cell layer in vivo on an implantable metallic stent having a lumen and a luminal surface, and an exterior surface. More specifically, the method includes implanting the stent with a coating in a patient in need of thereof; wherein the coating includes one or more layers of a matrix covalently adherent on said luminal and exterior surface of said stent containing one or more pharmaceutical substances on said exterior surface and a therapeutically effective amount of a single type of antibody, antibody fragments or combinations thereof being compatible to binding selectively to a specific cell surface antigen of circulating autologous endothelial progenitor cells in peripheral blood. In addition, genetically engineered endothelial progenitor cells can be captured on said luminal surface of stent in vivo, to proliferate to form rapidly a confluent endothelium in situ.

20 Claims, 2 Drawing Sheets

(51) Int. Cl.

| | | |
|---|---|---|
| *A61L 27/22* | (2006.01) | |
| *A61L 27/30* | (2006.01) | |
| *A61L 27/44* | (2006.01) | |
| *A61L 27/54* | (2006.01) | |
| *A61L 29/10* | (2006.01) | |
| *A61L 29/12* | (2006.01) | |
| *A61L 29/16* | (2006.01) | |
| *A61L 31/04* | (2006.01) | |
| *A61L 31/08* | (2006.01) | |
| *A61L 31/12* | (2006.01) | |
| *A61L 31/16* | (2006.01) | |
| *C12N 5/071* | (2010.01) | |
| *A61K 38/36* | (2006.01) | |
| *A61K 39/395* | (2006.01) | |
| *C07K 16/28* | (2006.01) | |
| *B82Y 30/00* | (2011.01) | |

(56) References Cited

U.S. PATENT DOCUMENTS

| | | | | |
|---|---|---|---|---|
| 5,811,447 | A * | 9/1998 | Kunz et al. | 514/411 |
| 5,830,879 | A * | 11/1998 | Isner | 514/44 R |
| 5,981,568 | A * | 11/1999 | Kunz et al. | 514/411 |
| 6,090,618 | A * | 7/2000 | Parmacek et al. | 435/320.1 |
| 6,171,609 | B1 * | 1/2001 | Kunz | 424/422 |
| 6,200,960 | B1 * | 3/2001 | Khachigian | 514/44 A |
| 6,238,872 | B1 * | 5/2001 | Mosseri | 435/7.1 |
| 6,258,787 | B1 * | 7/2001 | Isner | 514/44 R |
| 6,284,743 | B1 * | 9/2001 | Parmacek et al. | 514/44 R |
| 6,306,421 | B1 * | 10/2001 | Kunz et al. | 424/423 |
| 6,323,184 | B1 * | 11/2001 | Zalewski et al. | 514/44 R |
| 6,358,989 | B1 * | 3/2002 | Kunz et al. | 514/411 |
| 6,375,680 | B1 * | 4/2002 | Carlyle | 623/11.11 |
| 6,464,889 | B1 * | 10/2002 | Lee et al. | 216/37 |
| 6,515,009 | B1 * | 2/2003 | Kunz et al. | 514/411 |
| 6,544,541 | B1 * | 4/2003 | Zahradka | 424/422 |
| 7,186,882 | B2 * | 3/2007 | Mesaeli | 800/18 |
| 7,208,190 | B2 * | 4/2007 | Verlee et al. | 427/2.24 |
| 7,320,964 | B2 * | 1/2008 | Hecker et al. | 514/44 R |
| 7,563,278 | B2 * | 7/2009 | Flugelman | 623/1.41 |
| 7,597,764 | B2 * | 10/2009 | Verlee et al. | 118/667 |
| 7,959,942 | B2 * | 6/2011 | Cottone | 424/428 |
| 8,088,060 | B2 * | 1/2012 | Cottone et al. | 600/36 |
| 8,088,160 | B2 * | 1/2012 | Flugelman | 623/1.41 |
| 8,242,090 | B2 * | 8/2012 | Khachigian | 514/44 A |
| 8,257,725 | B2 * | 9/2012 | Cromack et al. | 424/423 |
| 8,431,145 | B2 * | 4/2013 | Toner et al. | 424/422 |
| 8,460,367 | B2 * | 6/2013 | Cottone et al. | 623/1.48 |
| 8,501,213 | B2 * | 8/2013 | Toner et al. | 424/422 |
| 8,642,068 | B2 * | 2/2014 | Cottone | 424/428 |
| 8,691,321 | B2 * | 4/2014 | Cottone | 427/2.24 |
| 2002/0019350 | A1 * | 2/2002 | Levine et al. | 514/12 |
| 2004/0072768 | A1 * | 4/2004 | Khachigian | 514/44 |
| 2004/0202773 | A1 * | 10/2004 | Verlee et al. | 427/2.1 |
| 2004/0254634 | A1 * | 12/2004 | Verlee et al. | 623/1.16 |
| 2005/0107870 | A1 * | 5/2005 | Wang et al. | 623/1.44 |
| 2005/0246009 | A1 * | 11/2005 | Toner et al. | 623/1.11 |
| 2005/0271701 | A1 * | 12/2005 | Cottone et al. | 424/426 |
| 2006/0223756 | A1 * | 10/2006 | Liau et al. | 514/16 |
| 2007/0123977 | A1 * | 5/2007 | Cottone et al. | 623/1.42 |
| 2007/0128723 | A1 * | 6/2007 | Cottone et al. | 435/402 |
| 2007/0129789 | A1 * | 6/2007 | Cottone et al. | 623/1.41 |
| 2007/0141107 | A1 * | 6/2007 | Kutryk et al. | 424/423 |
| 2008/0286316 | A1 * | 11/2008 | Kay | 424/278.1 |
| 2011/0110944 | A1 * | 5/2011 | Steidl et al. | 424/133.1 |
| 2012/0172970 | A1 * | 7/2012 | Cottone et al. | 623/1.15 |
| 2013/0035755 | A1 * | 2/2013 | Kutryk et al. | 623/1.38 |
| 2013/0295156 | A1 * | 11/2013 | Cottone et al. | 424/422 |
| 2014/0114401 | A1 * | 4/2014 | Consigny | 623/1.43 |
| 2014/0135901 | A1 * | 5/2014 | Cottone | 623/1.15 |

* cited by examiner

MEDICAL DEVICE WITH COATING THAT PROMOTES ENDOTHELIAL CELL ADHERENCE

This application is a continuation of U.S. patent application Ser. No. 11/562,931, filed Nov. 22, 2006, which is a continuation of U.S. patent application Ser. No. 10/832,106, filed Apr. 26, 2004, now U.S. Pat. No. 7,803,183, which is a continuation of U.S. patent application Ser. No. 09/808,867, filed Mar. 15, 2001, now U.S. Pat. No. 7,037,332, which claims benefit of U.S. Provisional Application No. 60/189,674 filed Mar. 15, 2000 and 60/201,789 filed May 4, 2000.

FIELD OF THE INVENTION

The present invention relates to the field of medical devices implanted in vessels within the body. More particularly, the present invention relates to stents or synthetic grafts implanted in blood vessels that incorporate a matrix which promotes adherence of endothelial cells to the stent or synthetic graft.

BACKGROUND OF THE INVENTION

Atherosclerosis is one of the leading causes of death and disability in the world. Atherosclerosis involves the deposition of fatty plaques on the lumenal surface of arteries. The deposition of fatty plaques on the lumenal surface of the artery causes narrowing of the cross-sectional area of the artery. Ultimately, this deposition blocks blood flow distal to the lesion causing ischemic damage to the tissues supplied by the artery Coronary arteries supply the heart with blood. Coronary artery atherosclerosis disease (CAD) is the most common, serious, chronic, life-threatening illness in the United States, affecting more than 11 million persons. The social and economic costs of coronary atherosclerosis vastly exceed that of most other diseases. Narrowing of the coronary artery lumen causes destruction of heart muscle resulting first in angina, followed by myocardial infarction and finally death. There are over 1.5 million myocardial infarctions in the United States each year. Six hundred thousand (or 40%) of those patients suffer an acute myocardial infarction and more than three hundred thousand of those patients die before reaching the hospital. (*Harrison's Principles of Internal Medicine*, 14$^{th}$ Edition, 1998).

CAD can be treated using percutaneous translumenal coronary balloon angioplasty (PICA) More than 400,000 PICA procedures are performed each year in the United States In PICA, a balloon catheter is inserted into a peripheral artery and threaded through the arterial system into the blocked coronary artery. The balloon is then inflated, the artery stretched, and the obstructing fatty plaque flattened, thereby increasing the cross-sectional flow of blood through the affected artery. The therapy, however, does not usually result in a permanent opening of the affected coronary artery. As many as 50% of the patients who are treated by PICA require a repeat procedure within six months to correct are narrowing of the coronary artery Medically, this re-narrowing of the artery after treatment by PTCA is called restenosis. Acutely, restenosis involves recoil and shrinkage of the vessel. Subsequently, recoil and shrinkage of the vessel are followed by proliferation of medial smooth muscle cells in response to injury of the artery from PICA. In part, proliferation of smooth muscle cells is mediated by release of various inflammatory factors from the injured area including thromboxane A$_2$ platelet derived growth factor (PDGF) and fibroblast growth factor (FGF). A number of different techniques have been used to overcome the problem of restenosis, including treatment of patients with various pharmacological agents or mechanically holding the artery open with a stent. (*Harrison's Principles of Internal Medicine*, 14$^{th}$ Edition, 1998).

Of the various procedures used to overcome restenosis, stents have proven to be the most effective. Stents are metal scaffolds that are positioned in the diseased vessel segment to create a normal vessel lumen Placement of the stent in the affected arterial segment prevents recoil and subsequent closing of the artery Stents can also prevent local dissection of the artery along the medial layer of the artery. By maintaining a larger lumen than that created using PICA alone, stents reduce restenosis by as much as 30% Despite their success, stents have not eliminated restenosis entirely. (Suryapranata et al 1998. Randomized comparison of coronary stenting with balloon angioplasty in selected patients with acute myocardial infarction. *Circulation* 97:2502-2502).

Narrowing of the arteries can occur in vessels other than the coronary arteries, including the aortoiliac, infrainguinal, distal profunda femoris, distal popliteal, tibial, subclavian and mesenteric arteries. The prevalence of peripheral artery atherosclerosis disease (PAD) depends on the particular anatomic site affected as well as the criteria used for diagnosis of the occlusion. Traditionally, physicians have used the test of intermittent claudication to determine whether PAD is present. However, this measure may vastly underestimate the actual incidence of the disease in the population Rates of PAD appear to vary with age, with an increasing incidence of PAD in older individuals Data from the National Hospital Discharge Survey estimate that every year, 55,000 men and 44,000 women had a first-listed diagnosis of chronic PAD and 60,000 men and 50,000 women had a first-listed diagnosis of acute PAD. Ninety-one percent of the acute PAD cases involved the lower extremity. The prevalence of comorbid CAD in patients with PAD can exceed 50%. In addition, there is an increased prevalence of cerebrovascular disease among patients with PAD.

PAD can be treated using percutaneous translumenal balloon angioplasty (PTA). The use of stents in conjunction with PTA decreases the incidence of restenosis. However, the post-operative results obtained with medical devices such as sterns do not match the results obtained using standard operative revascularization procedures, i.e., those using a venous or prosthetic bypass material. (*Principles of Surgery*, Schwartz et al. eds., Chapter 20, *Arterial Disease*, 7th Edition, McGraw-Hill Health Professions Division, New York 1999).

Preferably, PAD is treated using bypass procedures where the blocked section of the artery is bypassed using a graft. (*Principles of Surgery*, Schwartz et al. eds., Chapter 20, *Arterial Disease*, 7th Edition, McGraw-Hill Health Professions Division, New York 1999). The graft can consist of an autologous venous segment such as the saphenous vein or a synthetic graft such as one made of polyester, polytetrafluoroethylene (PTFE), or expanded polytetrafluoroethylene (ePTFE). The post-operative patency rates depend on a number of different factors, including the lumenal dimensions of the bypass graft, the type of synthetic material used for the graft and the site of outflow. Restenosis and thrombosis, however, remain significant problems even with the use of bypass grafts. For example, the patency of infrainguinal bypass procedures at 3 years using an ePTFE bypass graft is 54% for a femoral-popliteal bypass and only 12% for a femoral-tibial bypass.

Consequently, there is a significant need to improve the performance of both stents and synthetic bypass grafts in order to further reduce the morbidity and mortality of CAD and PAD.

With stents, the approach has been to coat the stents with various anti-thrombotic or anti-restenotic agents in order to reduce thrombosis and restenosis. For example, impregnating stents with radioactive material appears to inhibit restenosis by inhibiting migration and proliferation of myofibroblasts. (U.S. Pat. Nos. 5,059,166, 5,199,939 and 5,302,168). Irradiation of the treated vessel can pose safety problems for the physician and the patient In addition, irradiation does not permit uniform treatment of the affected vessel.

Alternatively, stents have also been coated with chemical agents such as heparin or phosphorylcholine, both of which appear to decrease thrombosis and restenosis. Although heparin and phosphorylcholine appear to markedly reduce restenosis in animal models in the short term, treatment with these agents appears to have no long term effect on preventing restenosis. Additionally, heparin can induce thrombocytopenia, leading to severe thromboembolic complications such as stroke. Nonetheless, it is not feasible to load stents with sufficient therapeutically effective quantities of either heparin or phosphorylcholine to make treatment of restenosis in this manner practical.

Synthetic grafts have been treated in a variety of ways to reduce postoperative restenosis and thrombosis (Bos et al 1998 Small-Diameter Vascular Graft Prostheses Current Status *Archives Physio, Biochem.* 106: 100~1 I 5). For example, composites of polyurethane such as meshed polycarbonate urethane have been reported to reduce restenosis as compared with ePTFE grafts The surface of the graft has also been modified using radiofrequency glow discharge to add polyterephalate to the ePTFE graft Synthetic grafts have also been impregnated with biomolecules such as collagen However, none of these approaches has significantly reduced the incidence of thrombosis or restenosis over an extended period of time.

Because endothelial cells possess certain intrinsic characteristics such as cell regulatory molecules that decrease the incidence of thrombosis or restenosis, stimulating the development of an endothelial cell monolayer on the surface of stents or synthetic grafts may prevent both restenosis and thrombosis. (Belle et al. 1997. Stent Endothelialization. *Circulation* 95:438-448, Bos et al. 1998 Small-Diameter Vascular Graft Prostheses Current Status *Archives Physio. Biochem.* 106:100-115)

Endothelial cells have been deposited on the surface of sterns by local delivery of vascular endothelial growth factor (VEGF), an endothelial cell mitogen, after implantation of the stent (Belle et al. 1997. Stent Endothelialization *Circulation* 95 438-448). Because the application of VEGF can have systemic as well as local effects, this form of treatment may be unreliable.

Synthetic grafts have also been seeded with endothelial cells, but the clinical results with endothelial seeding have been generally poor, i.e., low post-operative patency rates (Lio et al. 1998. New concepts and Materials in Microvascular Grafting: Prosthetic Graft Endothelial Cell Seeding and Gene Therapy. *Microsurgery* 18:263-256).

Accordingly, there is a need for development of new methods and compositions for coating medical devices, including stents and synthetic grafts, with endothelial cells. This type of coating will not only prevent restenosis, but also thromboembolic complications resulting from stent implantation. Methods and compositions that provide such improvement will eliminate the drawbacks of previous technology and have a significant positive impact on the morbidity and mortality associated with CAD and PAD. It is the object of this invention to prepare stents and synthetic grafts coated in such a manner as to stimulate adherence of endothelial cells to a medical device such as a stern or synthetic graft.

SUMMARY OF THE INVENTION

The invention provides methods and compositions for coating medical devices with a matrix that promotes adherence of endothelial cells to a medical device. The matrix incorporates antibodies that stimulate adherence of endothelial cells to the surface of the medical device.

As used herein, "medical device" refers to a device that is introduced temporarily or permanently into a mammal for the prophylaxis or therapy of a medical condition. These devices include any that are introduced subcutaneously, percutaneously or surgically to rest within an organ, tissue or lumen. Medical devices may include stents, covered stents such as those covered with polytetrafluoroethylene (PTFE), or expanded polytetrafluoroethylene (ePTFE), synthetic grafts, artificial heart valves, artificial hearts and fixtures to connect the prosthetic organ to the vascular circulation, venous valves, abdominal aortic aneurysm (AAA) grafts, inferior venal caval filters, permanent drug infusion catheters, embolic coils, embolic materials used in vascular embolization (e.g., PVA foams), and vascular sutures.

Coating of the medical device with the compositions and methods of this invention may stimulate the development of an endothelial cell layer on the surface of the medical device, thereby preventing restenosis as well as other thromboembolic complications that result from implantation of the medical device Synthetic grafts and stents can be used for treating CAD or PAD A stent or synthetic graft may be coated with a matrix incorporating antibodies that stimulate adherence of circulating progenitor endothelial cells to the medical device. The antibodies may comprise monoclonal antibodies reactive with endothelial cell surface antigens such as CD34, an antigen expressed on the surface of progenitor endothelial cells. Fab fragments of the monoclonal antibody may be used. In another embodiment, monoclonal antibodies directed against other endothelial surface antigens such as KDR or Tie-2, may also be used. In one embodiment, a single type of antibody that reacts with one antigen may be used. Alternatively, a plurality of different antibodies directed against different endothelial cell surface antigens may be mixed together and added to the matrix.

The matrix coating the medical device may be composed of synthetic material, such as polyurethane, poly-L lactic acid, cellulose ester or polyethylene glycol. In another embodiment, the matrix is composed of naturally occurring materials, such as collagen, fibrin, elastin or amorphous carbon. The matrix may comprise several layers with a first layer being composed of synthetic or naturally occurring materials and a second layer composed of antibodies. The layers may be ordered sequentially, with the first layer directly in contact with the stent or synthetic graft surface and the second layer having one surface in contact with the first layer and the opposite surface in contact with the vessel lumen.

In a third embodiment, the matrix may comprise fullerenes, where the fullerenes range from about C60 to about C100. The fullerenes may also be arranged as nanotubes, that incorporate molecules or proteins. The fullerene matrix may also be mixed with PTFE or ePTFE, or antibodies. Alternatively, the PTFE or ePTFE may be layered first on the medical device followed by a second layer of fullerenes.

The matrix may be noncovalently or covalently attached to the medical device. Antibodies may be covalently attached to the matrix using hetero- or homobifunctional cross-linking reagents.

Methods of treatment of atherosclerosis are also provided. The artery may be the either a coronary artery or a peripheral artery such as the femoral artery.

DETAILED DESCRIPTION OF THE INVENTION

Overview

Figure 1:
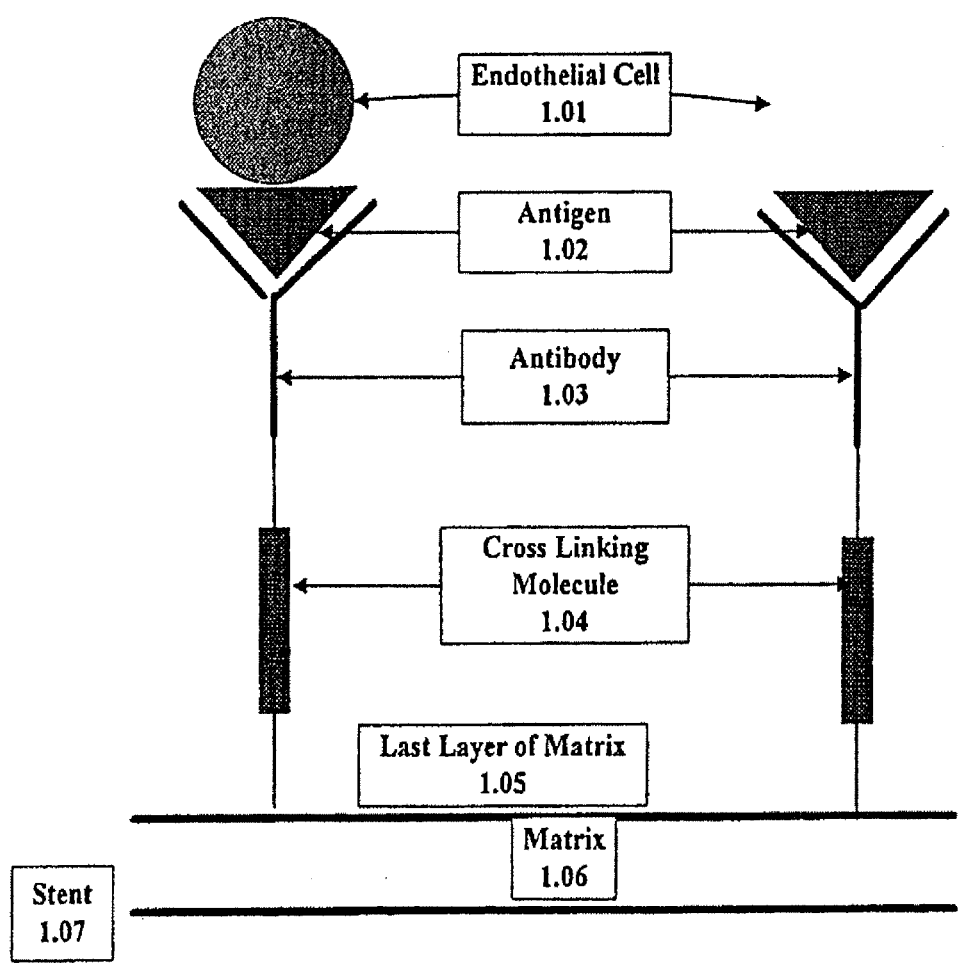
FIG. 1 shows an antibody tethered covalently to the matrix by a cross linking molecule.

The present invention provides methods and compositions that involve coating a medical device such as a stent or synthetic graft with a matrix which is then used to coat the medical device. In one embodiment, the matrix incorporates a therapeutically effective amount of at least one type of antibody that promotes adherence of endothelial cells to the medical device. Following adherence, the endothelial cells differentiate and proliferate on the surface of the matrix. The presence of endothelial cells on the medical device reduces the occurrence of restenosis and thrombosis after medical device implantation into a vessel.

As used herein, the term "antibody" refers to one type of monoclonal or polyclonal antibody, where the monoclonal or polyclonal antibody binds to one antigen or a functional equivalent of that antigen. The term antibody encompasses any fragment of an antibody such as Fab, $F(ab^1)_2$ or Fc fragments. (An antibody encompasses a plurality of individual antibody molecules equal to $6.022 \times 10^{23}$ molecules per mole of antibody).

As used herein, a "therapeutically effective amount of the antibody" means the amount of an antibody that promotes adherence of endothelial cells to the medical device. The amount of an antibody needed to practice the claimed invention varies with the nature of the antibody used. For example, the amount of an antibody used will depend on the binding constant between the antibody and the antigen against which it reacts. It is well known to those of ordinary skill in the art how to determine therapeutically effective amounts of an antibody to use with a particular antigen.

As used herein, "medical device" refers to a device that is introduced temporarily or permanently into a mammal for the prophylaxis or therapy of a medical condition These devices include any that are introduced subcutaneously, percutaneously or surgically to rest within an organ, tissue or lumen Medical devices may include, stents, covered stents such as those covered with PIPE, or ePTFE, synthetic grafts, artificial heart valves, artificial hearts and fixtures to connect the prosthetic organ to the vascular circulation, venous valves, abdominal aortic aneurysm (AAA) grafts, inferior venal caval filters, permanent drug infusion catheters, embolic coils, embolic materials used in vascular embolization (e.g., PVA foams), and vascular sutures.

As used herein, "restenosis' refers to the accumulation of a layer of smooth muscle cells and matrix protein in the intima of an arterial wall. Vessels may become obstructed because of restenosis. After PTCA or PTA, smooth muscle cells from the media and adventitia, which are not normally present in the intima, proliferate and migrate to the intima and secrete proteins, forming an accumulation of smooth muscle cells and matrix protein within the intima. This accumulation causes a narrowing of the lumen of the artery, reducing blood flow distal to the narrowing. As used herein, "inhibition of restenosis" refers to the inhibition of migration and proliferation of smooth muscle cells accompanied by prevention of protein secretion so as to prevent restenosis and the complications arising therefrom.

The subjects that can be treated using the methods and compositions of this invention may be a mammal, or more specifically, a human, dog, cat, pig, rodent or monkey.

The methods of the present invention may be practiced in vivo or in vitro.

The term "endothelial cell" refers to endothelial cells at any developmental stage, from progenitor to mature. Fully differentiated endothelial cells may be isolated from an artery or vein such as a human umbilical vein, while progenitor endothelial cells are isolated from peripheral blood or bone marrow. The endothelial cells are bound to the medical devices by incubation of the endothelial cells with a medical device coated with the matrix that incorporates an antibody or other agent that adheres to endothelial cells.

The methods of this invention may be practiced on any artery or vein. Included within the scope of this invention is atherosclerosis of any artery including coronary, infrainguinal, aortoiliac, subclavian, mesenteric and renal arteries. Other types of vessel obstructions, such as those resulting from a dissecting aneurysm are also encompassed by the invention.

The medical device may be coated with endothelial cells after insertion into a vessel. Alternatively, the medical device is coated with the endothelial cells before insertion of the medical device. In either case, the presence of endothelial cells on the lumenal surface of the medical device inhibits or prevents restenosis and thrombosis.

Endothelial Cells

Human umbilical vein endothelial cells (HUVEC) are obtained from umbilical cords according to the methods of Jaffe, et al., *J. Clin. Invest.*, 52:2745-2757, 1973, incorporated herein by reference. Briefly, cells are stripped from the blood vessel walls by treatment with collagenase and cultured in gelatin-coated tissue culture flasks in MI99 medium containing 10% low endotoxin fetal calf serum, 90 ug/ml preservative-free porcine heparin, 20 ug/ml endothelial cell growth supplement (ECGS), glutamine and antibodies.

Progenitor endothelial cells are isolated from human peripheral blood according to the methods of Asahara et al. (Isolation of putative progenitor endothelial cells for angiogenesis. Science 275:964-967, 1997, incorporated herein by reference). Magnetic beads coated with antibody to CD34 are incubated with human peripheral blood. After incubation, bound cells are eluted and can be cultured in M-199 containing 20% fetal bovine serum and bovine brain extract. (Clonetics, San Diego, Calif.). Cells are characterized by fluorescent antibodies to CD45, CD34, CD31, Flk-1, Tie-2, and E-selectin.

Endothelial cells are transfected with any mammalian expression vectors that contains any cloned genes encoding proteins such as platelet derived growth factor (PDGF), fibroblast growth factor (FGF), or nitric oxide synthase (NOS) using conventional methods. (See, for example, mammalian expression vectors and transfection kits commercially available from Stratagene, San Diego, Calif.). For example, purified porcine progenitor endothelial cells are transfected with vascular endothelial growth factor (VEGF) using an adenoviral expression vector expressing the VEGF cDNA according to the methods of Rosengart et al. (Six-month assessment of a phase I trial of angiogenic gene therapy for the treatment of coronary artery disease using direct intramyocardial administration of an adenovirus vector expressing the VEGF121 cDNA. *Ann. Surg.* 230(4):466-470 (1999), incorporated herein by reference).

Antibodies

Monoclonal antibodies useful in the method of the invention may be produced according to the standard techniques of Kohler and Milstein (Continuous cultures of fused cells secreting antibody of predefined specificity. Nature 265:495-497, 1975, incorporated herein by reference). Endothelial cells can be used as the immunogen to produce monoclonal antibodies directed against endothelial cell surface antigens.

Monoclonal antibodies directed against endothelial cells are prepared by injecting HUVEC or purified progenitor endothelial cells into a mouse or rat. After a sufficient time, the mouse is sacrificed and spleen cells are obtained. The spleen cells are immortalized by fusing them with myeloma cells or with lymphoma cells, generally in the presence of a non-ionic detergent, for example, polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity, i.e., reactivity with endothelial cell antigens.

Various techniques exist for enhancing yields of monoclonal antibodies such as injection of the hybridoma cells into the peritoneal cavity of a mammalian host which accepts the cells and then harvesting the ascites fluid. Where an insufficient amount of monoclonal antibody collects in the ascites fluid, the antibody is harvested from the blood of the host. Various conventional ways exist for isolation and purification of monoclonal antibodies so as to free the monoclonal antibodies from other proteins and other contaminants.

Also included within the scope of the invention are useful binding fragments of anti-endothelial cell monoclonal antibodies such as the Fab, F(ab$^1$)$_2$, or Fc fragments of these monoclonal antibodies. The antibody fragments are obtained by conventional techniques. For example, useful binding fragments may be prepared by peptidase digestion of the antibody using papain or pepsin.

Antibodies of the invention are directed to an antibody of the IgG class from a murine source; however, this is not meant to be a limitation. The above antibody and those antibodies having functional equivalency with the above antibody, whether from a murine source, mammalian source including human, or other sources, or combinations thereof are included within the scope of this invention, as well as other classes such as IgM, IgA, IgE, and the like, including isotypes within such classes. In the case of antibodies, the term "functional equivalency" means that two different antibodies each bind to the same antigenic site on an antigen, in other words, the antibodies compete for binding to the same antigen. The antigen may be on the same or different molecule.

In one embodiment, monoclonal antibodies reacting with the endothelial cell surface antigen CD34 are used. Anti-CD34 monoclonal antibodies attached to a solid support have been shown to capture progenitor endothelial cells from human peripheral blood. After capture, these progenitor cells are capable of differentiating into endothelial cells. (Ashara et al. 1997. Isolation of putative progenitor endothelial cells for angiogenesis. Science 275:964-967.) Hybridomas producing monoclonal antibodies directed against CD34 can be obtained from the American Type Tissue Collection. (Rockville, Md.). In another embodiment, monoclonal antibodies reactive with endothelial cell surface antigens Flk-1 or Tie-2 are used.

Polyclonal antibodies reactive against endothelial cells isolated from the same species as the one receiving the medical device implant may also be used.

Stent

The term "stent" herein means any medical device which when inserted into the lumen of a vessel expands the cross-sectional lumen of a vessel The term "stent" includes covered stents such as those covered with PTFE or ePTFE. In one embodiment, this includes stents delivered percutaneously to treat coronary artery occlusions or to seal dissections or aneurysms of the splenic, carotid, iliac and popliteal vessels. In another embodiment, the stent is delivered into a venous vessel. The stent can be composed of polymeric or metallic structural elements onto which the matrix is applied or the stent can be a composite of the matrix intermixed with a polymer. For example, a deformable metal wire stent can be used, such as that disclosed in U.S. Pat. No. 4,886,062 to Wiktor, incorporated herein by reference. A self-expanding stent of resilient polymeric material such as that disclosed in published international patent application WO91/12779 "Intraluminal Drug Eluting Prosthesis", incorporated herein by reference, can also be used. Stents may also be manufactured using stainless steel, polymers, nickel-titanium, tantalum, gold, platinum-iridium, or Elgiloy and MP35N and other ferrous materials. Stems are delivered through the body lumen on a catheter to the treatment site where the stent is released from the catheter, allowing the stent to expand into direct contact with the lumenal wall of the vessel. It will be apparent to those skilled in the art that other self-expanding stent designs (such as resilient metal stent designs) could be used with the antibodies and matrices of this invention.

Synthetic Graft

The term "synthetic graft" means any artificial prosthesis having biocompatible characteristics. In one embodiment this includes synthetic grafts made of Dacron (polyethylene terephthalate, PET) or Teflon (ePTFE). In another embodiment, synthetic grafts are composed of polyurethane. In yet a third embodiment, a synthetic graft is composed of an inner layer of meshed polycarbonate urethane and an outer layer of meshed Dacron. It will be apparent to those skilled in the art that any biocompatible synthetic graft can be used with the antibodies and matrices of this invention. (Bos et al. 1998. Small-Diameter Vascular Prostheses: Current Status. Archives Physio Biochem. 106:100-115, incorporated herein by reference). Synthetic grafts can be used for end-to-end anastomosis of vessels or for bypass of a diseased vessel segment.

Matrix (A) Synthetic Materials—The matrix that is used to coat the stent or synthetic graft may be selected from synthetic materials such as polyurethane, segmented polyurethane-urea/heparin, poly-L-lactic acid, cellulose ester or polyethylene glycol.

(B) Naturally Occurring Material—The matrix may be selected from naturally occurring substances such as collagen, laminin, heparin, fibrin, cellulose or carbon. A primary requirement for the matrix is that it be sufficiently elastic and flexible to remain unruptured on the exposed surfaces of the stent or synthetic graft.

(C) Fullerenes—The matrix may also comprise a fullerene (the term "fullerene" encompasses a plurality of fullerene molecules). Fullerenes are carbon-cage molecules. The number of carbon (C) molecules in a fullerene species varies from about C60 to about C100. Fullerenes are produced by high temperature reactions of elemental carbon or of carbon-containing species by processes well known to those skilled in the art; for example, by laser vaporization of carbon, heating carbon in an electric arc or burning of hydrocarbons in sooting flames. (U.S. Pat. No. 5,292,813, to Patel et al., incorporated herein by reference; U.S. Pat. No. 5,558,903 to Bhushan et al., incorporated herein by reference). In each case, a carbonaceous deposit or soot is produced. From this soot, various fullerenes are obtained by extraction with appropriate solvents, such as toluene. The fullerenes are separated by known methods, in particular by high performance liquid chromatography (HPLC). Fullerenes may be synthesized or obtained commercially from Dynamic Enterprises, Ltd., Berkshire, England or Southern Chemical Group, LLC, Tucker, Ga.

Fullerenes may be deposited on surfaces in a variety of different ways, including, sublimation, laser vaporization, sputtering, ion beam, spray coating, dip coating, roll-on or brush coating as disclosed in U.S. Pat. No. 5,558,903.

An important feature of fullerenes is their ability to form "activated carbon." The fullerene electronic structure is a system of overlapping pi-orbitals, such that a multitude of bonding electrons are cooperatively presented around the surface of the molecule. (*Chemical and Engineering News*, Apr. 8, 1991, page 59, incorporated herein by reference). As forms of activated carbon, fullerenes exhibit substantial van der Waals forces for weak interactions. The adsorptive nature of the fullerene surface may lend itself to additional modifications for the purpose of directing specific cell membrane interactions. For example, specific molecules that possess chemical properties that selectively bind to cell membranes of particular cell types or to particular components of cell membranes, e.g., lectins or antibodies, can be adsorbed to the fullerene surface. The fullerene surface may also be chemically modified to present specifically reactive groups to the cell membrane, e.g., oxidants or reductants. Attachment of different molecules to the fullerene surface may be manipulated to create surfaces that selectively bind various cell types, e.g., epithelial cells, fibroblasts, primary explants, or T-cell subpopulations. U.S. Pat. No. 5,310,669 to Richmond et al., incorporated herein by reference; Stephen R. Wilson, Biological Aspects of Fullerenes, *Fullerenes:Chemistry, Physics and Technology*, Kadish et al. eds., John Wiley & Sons, NY 2000, incorporated herein by reference.

Fullerenes may also form nanotubes that incorporate other atoms or molecules. (Liu et al. Science 280:1253-1256 (1998), incorporated herein by reference). The synthesis and preparation of carbon nanotubes is well known in the art. (U.S. Pat. No. 5,753,088 to Olk et al., and U.S. Pat. No. 5,641,466 to Ebbsen et al., both incorporated herein by reference). Molecules such as proteins may also be incorporated inside carbon nanotubes. For example, nanotubes may be filled with the enzymes, e.g., $Zn_2Cd_2$-metallothionein, cytochromes C and C3, and beta-lactamase after cutting the ends of the nanotube. (Davis et al. *Inorganica Chim. Acta* 272:261 (1998); Cook et al. *Full Sci. Tech.* 5(4):695 (1997), both incorporated herein by reference).

Three dimensional fullerene structures may also be used. U.S. Pat. No. 5,338,571 to Mirkin et al., incorporated herein by reference, discloses three-dimensional, multilayer fullerene structures that are formed on a substrate surface by (i) chemically modifying fullerenes to provide a bond-forming species; (ii) chemically treating a surface of the substrate to provide a bond-forming species effective to covalently bond with the bond-forming species of the fullerenes in solution; and, (iii) contacting a solution of modified fullerenes with the treated substrate surface to form a fullerene layer covalently bonded to the treated substrate surface.

(D) Application of the Matrix to the Medical Device

The matrix should adhere tightly to the surface of the stent or synthetic graft. Preferably, this is accomplished by applying the matrix in successive thin layers. Each layer of matrix may incorporate the antibodies. Alternatively, antibodies may be applied only to the layer in direct contact with the vessel lumen. Different types of matrices may be applied successively in succeeding layers. The antibodies may be covalently or noncovalently coated on the matrix after application of the matrix to the stent.

In order to coat a medical device such as a stent, the stent is dipped or sprayed with a liquid solution of the matrix of moderate viscosity. After each layer is applied, the stent is dried before application of the next layer. In one embodiment, a thin, paint-like matrix coating does not exceed an overall thickness of 100 microns.

For example, a suitable matrix coating solution is prepared by dissolving 480 milligrams (mg) of a drug carrier, such as poly-D, L-lactid (available as 8203 of Boehringer Inc., Ingelheim, Germany) in 3 milliliters (ml) of chloroform under aseptic conditions. In principle, however, any biodegradable (or non-biodegradable) matrix that is blood- and tissue-compatible (biocompatible) and can be dissolved, dispersed or emulsified may be used as the matrix if after application, it undergoes relatively rapid drying to a self-adhesive lacquer- or paint-like coating on the medical device.

For example, coating a stent with fibrin is well known to one of ordinary skill in the art. In U.S. Pat. No. 4,548,736 issued to Muller et al., incorporated herein by reference, fibrin is clotted by contacting fibrinogen with thrombin. Preferably, the fibrin in the fibrin-containing gent of the present invention has Factor XIII and calcium present during clotting, as described in U.S. Pat. No. 3,523,807 issued to Gerendas, incorporated herein by reference, or as described in published European Patent Application 0366564, incorporated herein by reference, in order to improve the mechanical properties and biostability of the implanted device. Preferably, the fibrinogen and thrombin used to make fibrin in the present invention are from the same animal or human species as that in which the gent will be implanted in order to avoid any inter-species immune reactions, e.g., human anti-cow. The fibrin product can be in the form of a fine, fibrin film produced by casting the combined fibrinogen and thrombin in a film and then removing moisture from the film osmotically through a semipermeable membrane. In the European Patent Application 0366564, a substrate (preferably having high porosity or high affinity for either thrombin or fibrinogen) is contacted with a fibrinogen solution and with a thrombin solution. The result is a fibrin layer formed by polymerization of fibrinogen on the surface of the medical device. Multiple layers of fibrin applied by this method could provide a fibrin layer of any desired thickness. Alternatively, the fibrin can first be clotted and then ground into a powder which is mixed with water and stamped into a desired shape in a heated mold (U.S. Pat. No. 3,523,807). Increased stability can also be achieved in the shaped fibrin by contacting the fibrin with a fixing agent such as glutaraldehyde or formaldehyde. These and other methods known by those skilled in the art for making and forming fibrin may be used in the present invention.

If a synthetic graft is coated with collagen, the methods for preparing collagen and forming it on synthetic graft devices are well known as set forth in U.S. Pat. No. 5,851,230 to Weadock et al., incorporated herein by reference. This patent describes methods for coating a synthetic graft with collagen. Methods for adhering collagen to a porous graft substrate typically include applying a collagen dispersion to the substrate, allowing it to dry and repeating the process. Collagen dispersions are typically made by blending insoluble collagen (approximately 1-2% by weight) in a dispersion at acidic pH (a pH in a range of 2 to 4). The dispersion is typically injected via syringe into the lumen of a graft and massaged manually to cover the entire inner surface area with the collagen slurry. Excess collagen slurry is removed through one of the open ends of the graft. Coating and drying steps are repeated several times to provide sufficient treatment.

In yet another embodiment, the stent or synthetic graft is coated with amorphous carbon. In U.S. Pat. No. 5,198,263, incorporated herein by reference, a method for producing a high-rate, low-temperature deposition of amorphous carbon films in the presence of a fluorinated or other halide gas is described. Deposition according to the methods of this invention can be performed at less than 100° C., including ambient room temperature, with a radio-frequency, plasma-assisted, chemical-vapor deposition process. The amorphous carbon film produced using the methods of this invention adheres well to many types of substrates, including for example glasses, metals, semiconductors, and plastics.

Attachment of a fullerene moiety to reactive amino group sites of an amine-containing polymer to form the fullerene-graft, amine-containing polymers may be performed as described in U.S. Pat. No. 5,292,813. Chemical modification in this manner allows for direct incorporation of the fullerenes into the stent. In another embodiment, the fullerenes may be deposited on the surface of the stent or synthetic grafts as described above. (see, WO 99/32184 to Leone et al., incorporated by reference). Fullerenes may also be attached through an aldehyde bond (Yamago et al., Chemical Derivatization of Organofullerenes through Oxidation, Reduction and C-0 and C—C Bond Forming Reactions. J. Org. Chem., 58 4796-4798 (1998), incorporated herein by reference). C600 may also be attached directly through an epoxide group on the fullerene to a stent. The attachment is through a covalent linkage to the oxygen. This compound and the protocols for coupling are commercially available from BuckyUSA. (BuckyUSA, Houston, Tex.).

(E) Addition of Antibodies to the Matrix—Antibodies that promote adherence of progenitor endothelial cells can be incorporated into the matrix, either covalently or noncovalently. Antibodies may be incorporated into each layer of matrix by mixing the antibodies with the matrix coating solution. Alternatively, the antibodies may be covalently or noncovalently coated on to last layer of matrix that is applied to the medical device.

In one embodiment, the antibodies are added to a solution containing the matrix. For example, Fab fragments on anti-CD34 monoclonal antibody are incubated with a solution containing human fibrinogen at a concentration of between 500 and 800 mg/dl. It will be appreciated that the concentration of anti-CD34 Fab fragment will vary and that one of ordinary skill in the art could determine the optimal concentration without undue experimentation. The stent is added to the Fab/fibrin mixture and the fibrin activated by addition of concentrated thrombin (at a concentration of at least 1000 U/ml). The resulting polymerized fibrin mixture containing the Fab fragments incorporated directly into the matrix is pressed into a thin film (less than 0.12 cm) on the surface of the stent or synthetic graft. Virtually any type of antibody or antibody fragment can be incorporated in this manner into a matrix solution prior to coating of agent or synthetic graft.

In another embodiment, antibodies are covalently coupled to the matrix. In one embodiment, the antibodies are tethered covalently to the matrix through the use of hetero- or homo-bifunctional linker molecules. As used herein the term "tethered" refers to a covalent coupling of the antibody to the matrix by a linker molecule. The use of linker molecules in connection with the present invention typically involves covalently coupling the linker molecules to the matrix after it is adhered to the stent. After covalent coupling to the matrix, the linker molecules provide the matrix with a number of functionally active groups that can be used to covalently couple one or more types of antibody. FIG. 1 provides an illustration of coupling via a cross-linking molecule. An endothelial cell, 1.01, binds to an antibody, 1.03, by a cell surface antigen, 1.02. The antibody is tethered to the matrix, 1.05-1.06, by a cross-linking molecule, 1.04. The matrix, 1.05-1.06, adheres to the stent, 1.07. The linker molecules may be coupled to the matrix directly (i.e., through the carboxyl groups), or through well-known coupling chemistries, such as, esterification, amidation, and acylation. The linker molecule may be a di- or tri-amine functional compound that is coupled to the matrix through the direct formation of amide bonds, and provides amine-functional groups that are available for reaction with the antibodies. For example, the linker molecule could be a polyamine functional polymer such as polyethyleneimine (PEI), polyallylamine (PALLA) or polyethyleneglycol (PEG). A variety of PEG derivatives, e.g., mPEG-succinimidyl propionate or mPEG-N-hydroxysuccinimide, together with protocols for covalent coupling, are commercially available from Shearwater Corporation, Birmingham, Ala. (See also, Weiner et al., Influence of a polyethyleneglycol spacer on antigen capture by immobilized antibodies. *J. Biochem. Biophys. Methods* 45:211-219 (2000), incorporated herein by reference). It will be appreciated that the selection of the particular coupling agent may depend on the type of antibody used and that such selection may be made without undue experimentation. Mixtures of these polymers can also be used. These molecules contain a plurality of pendant amine-functional groups that can be used to surface-immobilize one or more antibodies.

Figure 2:
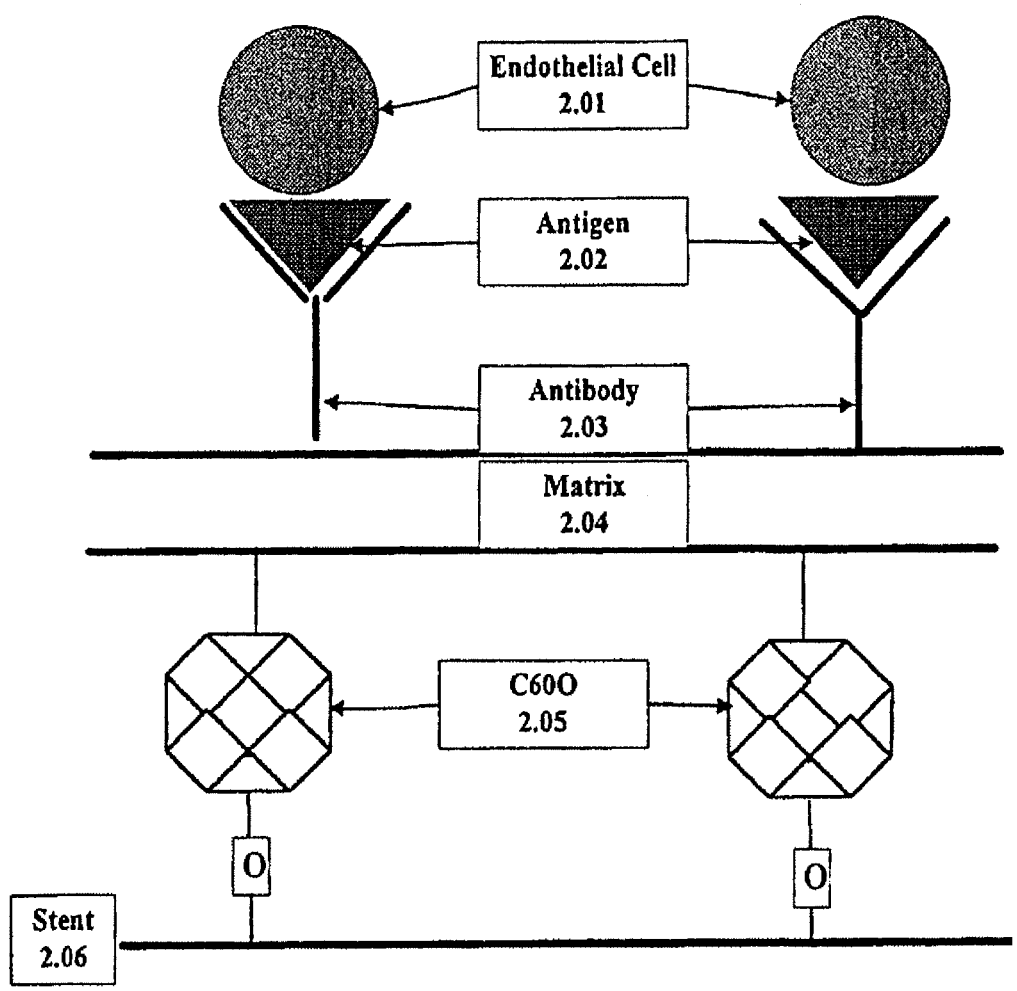
FIG. 2 shows a diagram of the C600 molecule anchoring the matrix

Antibodies may be attached to C600 fullerene layers that have been deposited directly on the surface of the stent. Cross linking agents may be covalently attached to the fullerenes. The antibodies are then attached to the cross-linking agent, which in turn is attached to the stent. FIG. 2 provides an illustration of coupling by C600. The endothelial cell, 2.01, is bound via a cell surface antigen, 2.02, to an antibody, 2.03, which in turn is bound, covalently or non-covalently to the matrix, 2.04. The matrix, 2.04, is coupled covalently via C600, 2.05, to the stent, 2.06.

EXPERIMENTAL EXAMPLES

This invention is illustrated in the experimental details section which follows. These sections set forth below the understanding of the invention, but are not intended to, and should not be construed to, limit in any way the invention as set forth in the claims which follow thereafter.

Example 1

Adherence of Human Endothelial Cells to CD34 Fab-Coated Stents

Materials and Methods
1. Cells
HUVEC will be prepared from human umbilical cords by the method of Jaffe (Jaffe, E. A. In "*Biology of Endothelial Cells*", E. A. Jaffe, ed., Martinus-Nijhoff, The Hague (1984), incorporated herein by reference) and cultured in Medium 199 supplemented with 20% fetal calf serum (FCS), L-glutamine, antibiotics, 130 ug/ml heparin and 1.2 mg/ml endothelial cell growth supplement (Sigma-Aldrich, St. Louis, Mo.).

Progenitor endothelial cells will be isolated from human peripheral blood by the method of Asahara et al. (Isolation of Putative progenitor endothelial cells for angiogenesis. *Science* 275:964-967). Monoclonal anti-CD34 antibodies will be coupled to magnetic beads and incubated with the leukocyte fraction of human whole blood. After incubation, bound cells will be eluted and cultured in M-199 containing 20% fetal bovine serum and bovine brain extract. (Clonetics, San Diego, Calif.). Cells will be characterized by fluorescent antibodies to CD45, CD34, CD31, Flk-1, Tie-2, and E-selectin.

2. Coating of Stents

A. R stents produced by Orbus International B. V. (Leusden, The Netherlands) will be incubated with human fibrinogen (Sigma, St. Louis, Mo.) 500-800 mg/ml together with Fab fragments of anti-CD34 monoclonal antibody and the fibrinogen will be polymerized by the addition of 1000 units/ml of thrombin. After incubation of the stent with the polymerized fibrin mixture containing the anti-CD34 monoclonal Fab fragments, the fibrin will be compressed into a thin film (less than 0.012 cm) against the R Stent. The R-Stent having the thin, fibrin film containing the Fab fragments will be washed three times with phosphate-buffered saline (PBS) containing 0.5% bovine serum albumin (BSA) at room temperature.

B. Alternatively, R stents will be coated with mPEG-succinimidyl propionate (Shearwater Corporation, Birmingham, Ala.). The succinimidyl group will be reacted with the anti-CD34 monoclonal Fab fragments (Fab-PEG coated R stents) according to the manufacturer's instructions to form a stable amide linkage between the PEG derivative and the Fab fragment.

3. Endothelial Cell Binding Assay

The fibrin-anti-CD34 Fab coated R-stents or Fab-PEG coated R stents will be incubated with isolated HUVEC or isolated progenitor endothelial cells at cellular concentrations of between 100,000 and 1,000,000 cells/ml in M199 containing 0.5% BSA at 37° C. in a 5% CO2 humidified atmosphere. Prior to incubation with the stent, the HUVEC or progenitor endothelial cells will be labeled with [$^3$H]-thymidine for 24 hours. After incubation of the labeled endothelial cells with the stents coated with fibrin and Fab anti-CD34 for between 4 and 72 hours, the stents will be removed from the solution and washed 5 times with M199 containing 0.5% BSA. Bound endothelial cells will be removed by trypsinization and binding of labeled endothelial cells to the stents will be assessed by scintillation counting of [3H]-thymidine. As negative control, stents coated with fibrin alone or uncoated stents will be incubated with [311]-thymidine-labeled endothelial cells. Results will be evaluated statistically using a t-test to determine differential binding. Stents coated with fibrin which incorporate monoclonal anti-CD34 Fab fragments will show significantly increased binding of endothelial cells as compared with uncoated stents.

Example 2

Proliferation of Human Endothelial Cells on CD34 FAB-Coated Stents

Endothelial Cell Proliferation Assay

R stents coated with fibrin that incorporates anti-CD34 Fab fragments will be incubated with HUVEC or progenitor endothelial cells for between 4 and 72 hours in M199 containing 0.5% BSA. After incubation of the stents with the HUVEC or progenitor endothelial cells, the stents will be washed 5 times with M199 containing 0.5% BSA and then incubated with [$^3$H]-thymidine. [$^3$H]-thymidine incorporation will be assessed in washed and harvested HUVEC or progenitor endothelial cells (cells will be harvested with trypsin). Proliferation of HUVEC or progenitor endothelial cells on fibrin-coated stents will be compared with endothelial cell proliferation in standard microtiter dishes. Proliferation of HUVEC or progenitor endothelial cells on fibrin-coated stents will be equal to or greater than proliferation of endothelial cells in microtiter dishes Example 3

Production of Monoclonal Antibodies Reactive with HUVEC and Progenitor Endothelial Cells BALB/c mice will be immunized, intraperitoneally 3-4 times at 2-4 weekly intervals, with $1.5 \times 10^6$ HUVEC in PBS or $1.5 \times 10^6$ progenitor endothelial cells and challenged 3 days prior to spleen-cell removal with $1.5 \times 10^6$ HUVEC or $1.5 \times 10^6$ progenitor endothelial cells. A spleen-cell suspension will be prepared, fused with the myeloma NS1/1 AG4.1 and hybridomas grown up and cloned. To improve hybridoma growth and cloning efficiencies, 10% endothelial-cell conditioned medium (HUVEC) will be included in culture media. Initially, hybridoma culture supernatants will be tested for reactivity with HUVEC or progenitor endothelial cells by immunofluorescence flow cytometry (FACS). Briefly, HUVEC ($1.5 \times 10^4$) or progenitor endothelial cells ($1.5 \times 10^4$) will be incubated (30 min, 4° C.) with undiluted hybridoma supernatant, washed and incubated with fluorescein-isothiocyanate (FITC)-sheep F(ab$^1$)$_2$ anti-mouse Ig (100 ug/ml). Following final washing, the endothelial cells will be examined for monoclonal antibody binding by FACS analysis. Positive hybridoma supernatants will be screened on the human melanoma cell line MM-170 to eliminate non-endothelial specific mAbs. Endothelial specificity will be further confirmed by screening of monoclonal antibodies on a panel of human tumor cell lines as well as human lymphocytes, monocytes, neutrophils, red cells and platelets.

Example 4

Porcine Balloon Injury Studies

Implantation of antibody-covered stents will be performed in juvenile Yorkshire pigs weighing between 25 and 30 kg. Animal care will comply with the "Guide for the Care and Use of Laboratory Animals" (NIH publication No, 80-23, revised 1985). After an overnight fast, animals will be sedated with ketamine hydrochloride (20 mg/kg). Following the induction of anesthesia with thiopental (12 mg/kg) the animals will be intubated and connected to a ventilator that will administer a mixture of oxygen and nitrous oxide (1:2 (vol/vol]). Anesthesia will be maintained with 0.5-2.5 vol % isoflurane. Antibiotic prophylaxis will be provided by an intramuscular injection of 1,000 mg of a mixture of procaine penicillin-G and benzathine penicillin-G (streptomycin).

Under sterile conditions, an arteriotomy of the left carotid artery will be performed and a 9F-introducer sheath will be placed in the left carotid artery. All animals will be given 7,500 IU of heparin sodium and 100 mg of acetylsalicylic acid intravenously. Additional 2,500 IU boluses of heparin will be administered periodically throughout the procedure in order to maintain an activated clotting time above 300 seconds. An 8F guiding catheter will be introduced through the carotid sheath and passed to the origin of the iliac artery. Angiography will be performed after the administration of I mg of isosorbide dinitrate and images will be analyzed using a quantitative coronary angiography system. A 3F-embolectomy catheter will be inserted into the common femoral artery, and passed distal to the segment selected for stent implantation. The embolectomy balloon will be inflated to a size 0.5 mm larger than the arterial segment and withdrawn twice to denude the vessel. Immediately after denudation, a fibrin-coated stent incorporating an Fab fragment of a monoclonal antibody will be inserted through the guiding catheter and deployed in the denuded segment of the femoral artery. Animals will be sacrificed both at 3 days and at eight weeks after stent implantation. The animal will first be sedated and anesthetized as described above. The stented femoral segments will be explanted and then placed in 4% paraformaldehyde in 0.1 M phosphate buffer pH 7.2 at C for 48 h. A rectangular section of the vessel wall will be removed for further processing for electron microscopic evaluation of surface coverage of endothelial cells. This portion of the stented vessel will be placed in 0.15 cacodylate buffer and further fixed with 2.5% glutaraldehyde in 0.15 M cacodylate. The tissue will then be post-fixed with 0.1 M cacodylate buffer containing 1% $OsO_4$ and 50 mM ferricyanide ($K_3[Fe(CN)_6]$), and further processed. (Reduction in thrombotic events with heparin-coated Palmaz-Schatz stents in normal porcine coronary arteries, Circulation 93:423.430, incorporated herein by reference).

The remaining sections of the stented arterial segments will be impregnated with three changes of methy methacrylate as described by van Beusekom et al. (Cardiovasc Pathol 5:69-76 (1996), incorporated herein by reference). Embedded arterial segments with the stent in place will be cut into sections 3 to 5 gm thick on a motor-driven rotary microtome (HM-350, Microm GmbH, Munich, Germany) using stainless steel disposable knives. On chrome aluminum coated slides, sections will be stretched on a hot plate at 40° C. using a mixture of 60% 2-butoxyethanol and 10% ethanol in water. Sections will be covered by a plastic film, excess butoxyethanol-ethanol mixture removed and the slides will be left overnight to dry in a 40° C. oven. Sections will then be deplasticized in a solution of equal volumes of xylene-chloroform for 30 to 60 minutes. Standard staining procedures for light microscopy will then be performed on the prepared sections. Statistics: Data will be presented as the mean±standard error of the mean (SD) of the independent experiments. Statistical significance will be determined by one way analysis of variance (ANOVA) and Fisher's PLSD test (StatView 4.01; Brain Power, Inc., Calabasas, Calif.). For data of treated and untreated segments of femoral arteries, a paired t test (StatView 4.01) will be used. A p value of <0.05 will be considered a statistically significant difference between the means. Animals treated with a stent incorporating an anti-porcine endothelial cell monoclonal Fab fragment will show increased endothelial cell coverage and significantly reduced restenosis as compared with controls having an uncoated gent implanted.

Example 5

Transfection of Porcine Progenitor Endothelial Cells

Porcine progenitor endothelial cells will be isolated from pig peripheral blood by the method of Asahara et al. (Isolation of Putative progenitor endothelial cells for angiogenesis. *Science* 275:964-967). Monoclonal anti-CD34 antibodies will be coupled to magnetic beads and incubated with the leukocyte fraction of pig whole blood. After incubation, bound cells will be eluted and cultured in M-199 containing 20% fetal bovine serum and bovine brain extract. (Clonetics, San Diego, Calif.). Cells will be characterized by fluorescent antibodies to CD45, CD34, CD31, Flk-1, Tie-2, and E-selectin.

For example, purified porcine progenitor endothelial cells will be transfected with vascular endothelial growth factor (VEGF) using an adenovirus vector expressing the VEGF cDNA according to the methods of Rosengart et al. (Six-month assessment of a phase I trial of angiogenic gene therapy for the treatment of coronary artery disease using direct intramyocardial administration of an adenovirus vector expressing the VEGF121 cDNA. *Ann. Surg.* 230(4):466-470 (1999), incorporated herein by reference).

The transfected purified porcine progenitor cells expressing VEGF will be infused into the porcine femoral artery model after balloon injury and stent implantation as described in Example 4 using a double-balloon chamber infusion catheter (Cordis Corp) which isolates the stented portion of the femoral artery. Restenosis will be compared in balloon angioplasty stent-treated pigs infused with VEGF-transfected porcine progenitor cells as compared with pigs infused With un-transfected porcine progenitor endothelial cells. Expression of VEGF in the re-infused porcine progenitor endothelial cells will result in a decreased incidence and severity of restenosis in the anti-CD34 coated stents.

Example 6

Preparation of Aminosilane PEO Tethered Antibodies

Stent Preparation—stents will be made from 316 L stainless steel and will be cleaned and passivated by first washing in an anionic detergent in an ultrasonic cleaner and then soaked in hot nitric acid with agitation, followed by a final deionized water rinse.

Derivatized stents will be prepared as follows—stents will be dipped into a 2% mixture of N-(2-arninoethyl-3-aminopropyl) trimethoxysilane in 95% ethanol for three minutes, removed, air dried at room temperature and then cured for 10 minutes at 110° C.

Polyethylene glycol (PEG) Spacer Coupling—Derivatized stents will be placed in 100 ml of 0.1M MES buffer containing 10 mM Dicarboxymethyl-PEG and 500 mg of EDC added and incubated at 25° C. with constant stirring for two hours.

Tethered Antibody—Antibodies to endothelial cells will be immobilized to the PEG functionalized stents in a one-step carbodiimide coupling reaction by immersing the stents into 150 ml of 0.1M MES buffer (pH 4.5) into which 1.0 mg of marine anti-CD34 $IgG_1$ antibody is dissolved and incubated at 25° C. for two hours. Stents will be removed from the solution and rinsed five times with 50 ml of phosphate buffered saline (pH 7.2) with 0.02% Tween 20.

Reagents include: N-(2-aminoethyl-3-aminopropyl)trimethoxysilane (Degussa-Hula); MES buffer—morpholine ethane sulfonic acid buffer (Sigma, St. Louis, Mo.); EDC ethyl-3-(3-dimethylaminopropyl) carbodiimide (Sigma, St. Louis, Mo.); Dicarboxymethyl-PEG-Dicarboxymethyl-poly (ethylene glycol) [MW 3400] (Shearwater, Huntsville, Ala.).

Having described several different embodiments of the invention, it is not intended that the invention is limited to these embodiments it is intended that modifications and variations may be made by one skilled in the art without departing from the spirit and scope of the invention as defined in the claims.

We claim:

1. A method for delivering a stent into a patient, the method comprising the step of:

implanting a stent with a coating to a patient in need of said stent; wherein said coating comprises one or more layers of a matrix attached to said stent;

said one or more layers of the matrix containing one or more pharmaceutical substances, wherein the pharmaceutical substance inhibits smooth muscle cell proliferation and/or migration; and wherein the coating further comprises a therapeutically effective amount of an antibody, antibody fragments or combinations thereof, and wherein said antibody, antibody fragments or combinations thereof specifically binds to a cell surface antigen of endothelial progenitor cells or endothelial cells in peripheral blood.

2. The method of claim 1, wherein the antibody, antibody fragments or combinations thereof is/are immobilized to one or more layers of a biocompatible matrix.

3. The method of claim 2, wherein the one or more layers of said biocompatible matrix are bioabsorbable or non-absorbable.

4. The method of claim 1, wherein the antibody, antibody fragments or combinations thereof specifically binds to genetically engineered stem or progenitor cells.

5. The method of claim 1, wherein said one or more layers of said matrix further comprises molecules for inducing proliferation or differentiation of captured circulating stem cells or progenitor cells or genetically engineered cells, in situ.

6. The method of claim 1, wherein said one or more layers of said matrix is formed of a natural or synthetic polymer.

7. The method of claim 6, wherein said synthetic polymer is polyurethane, segmented polyurethane-urea/heparin, polylactic acid, cellulose ester, polyethylene glycol, or combinations thereof.

8. The method of claim 6, wherein said natural polymer is collagen, laminin, heparin, fibrin, cellulose, elastin or combinations thereof.

9. The method of claim 1, wherein said one or more layers of said matrix are a fibrous mesh.

10. The method of claim 1, wherein the specific antibody, antibody fragment or combination thereof bind an antigen selected from CD45, CD34, CD31, Flk-1, Tie-2, and E-selectin.

11. The method of claim 1, wherein the endothelial progenitor cells or endothelial cells are transfected with a mammalian expression vector.

12. The method of claim 11, wherein the mammalian expression vector comprises one or more cloned genes encoding a protein selected from the group consisting of platelet derived growth factor (PDGF), fibroblast growth factor (FGF), and nitric oxide synthase.

13. The method of claim 1, wherein said one or more layers of said matrix comprises a synthetic polymer, naturally occurring polymer, fullerenes or amorphous carbon.

14. The method of claim 1, wherein the antibodies or antibody fragments are derived from monoclonal antibodies or fragments thereof.

15. The method of claim 1, wherein the antibodies or antibody fragments have specificity to bind an endothelial cell membrane antigen.

16. The method of claim 1, wherein said coating promotes in vivo adherence of circulating endothelial cells to said medical device.

17. The method of claim 1, wherein the coating comprises at least one layer of a synthetic matrix and the antibodies are anti-CD34 antibodies.

18. The method of claim 1, wherein the stent comprises stainless steel, nickel-titanium, tantalum, gold, platinum-iridium, Elgiloy, or MP35N.

19. A method of claim 1, wherein the antibodies, antibody fragments or combinations thereof comprise a plurality of different antibodies directed against different specific endothelial cell surface antigens.

20. The method of claim 1, wherein the one or more layers of the matrix comprise a material selected from the group consisting of a fullerene, polyurethane, segmented polyurethane-urea/heparin, poly(D,L-lactide), poly-L-lactic acid, cellulose ester, polyethylene glycol, collagen, elastin, laminin, heparin, fibrin, cellulose, carbon, polytetrafluoroethylene, and expanded polytetrafluoroethylene.

* * * * *

UNITED STATES PATENT AND TRADEMARK OFFICE
CERTIFICATE OF CORRECTION

PATENT NO.         : 9,072,723 B2
APPLICATION NO.    : 13/589907
DATED              : July 7, 2015
INVENTOR(S)        : Michael John Bradley Kutryk, Robert John Cottone, Jr. and Stephen Maxwell Rowland It is certified that error appears in the above-identified patent and that said Letters Patent is hereby corrected as shown below:

Title page, item (73) Assignee "ORBUS MEDICAL TECHNOLOGY INC, Fort Lauderdale, FL (US)" should read -- OrbusNeich Medical, Inc., Fort Lauderdale, FL (US) --

Signed and Sealed this
Fifth Day of April, 2016

Michelle K. Lee
*Director of the United States Patent and Trademark Office*